(12) United States Patent
Zirkle et al.

(10) Patent No.: US 11,337,752 B2
(45) Date of Patent: *May 24, 2022

(54) IRRIGATED CATHETER WITH INTERNAL POSITION SENSOR

(71) Applicant: BIOSENSE WEBSTER, INC., Irvine, CA (US)

(72) Inventors: Michael Olen Zirkle, Yorba Linda, CA (US); Jeffrey L. Clark, Castaic, CA (US)

(73) Assignee: BIOSENSE WEBSTER, INC., Irvine, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/391,179

(22) Filed: Apr. 22, 2019

(65) Prior Publication Data

US 2019/0247115 A1 Aug. 15, 2019

Related U.S. Application Data

(63) Continuation of application No. 15/960,402, filed on Apr. 23, 2018, now Pat. No. 10,265,124, which is a
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/283* (2021.01); *A61B 5/6852* (2013.01);
(Continued)

(58) Field of Classification Search
CPC ...... A61B 18/1492; A61B 2018/00011; A61B 2018/00029; A61B 2034/2051;
(Continued)

(56) References Cited

U.S. PATENT DOCUMENTS

| 4,770,171 A | 9/1988 | Sweren et al. |
| 5,391,199 A | 2/1995 | Ben-Haim |

(Continued)

FOREIGN PATENT DOCUMENTS

| CN | 101528145 A | 9/2009 |
| EP | 0 956 826 A2 | 11/1999 |

(Continued)

OTHER PUBLICATIONS

Partial European Search Report completed Sep. 24, 2009, for European Patent Application No. 09251788.7, 8 pages.
(Continued)

*Primary Examiner* — Khadijeh A Vahdat
(74) *Attorney, Agent, or Firm* — Lewis Roca Rothgerber Christie LLP

(57) ABSTRACT

A catheter carries a position sensor in a distal, on-axis position in an irrigated ablation tip electrode. The tip electrode has a shell wall that defines a cavity through which fluid flows and exits via fluid ports formed in the shell wall. The cavity is sealed by an internal member extends into the cavity with a baffle portion and a distal portion. The distal portion safely houses the position sensor and the baffle portion diffuses and disperses fluid entering the tip electrode for a more uniform flow through the cavity. The distal portion is configured to provide an annular region that runs along the length of the tip electrode to better feed fluid to the more distal fluid ports on the tip electrode for more uniform cooling at all locations on the tip electrode.

19 Claims, 12 Drawing Sheets

Related U.S. Application Data continuation of application No. 12/767,763, filed on Apr. 26, 2010, now Pat. No. 9,949,791.

(51) Int. Cl.

| | |
|---|---|
| *A61M 25/01* | (2006.01) |
| *A61B 5/283* | (2021.01) |
| *A61B 18/00* | (2006.01) |
| *A61B 34/20* | (2016.01) |
| *A61B 5/287* | (2021.01) |

(52) U.S. Cl.
CPC .... *A61M 25/0136* (2013.01); *A61M 25/0147* (2013.01); *A61B 5/287* (2021.01); *A61B 34/20* (2016.02); *A61B 2018/00011* (2013.01); *A61B 2018/00029* (2013.01); *A61B 2034/2051* (2016.02); *A61B 2218/002* (2013.01)

(58) Field of Classification Search
CPC ... A61B 2218/002; A61B 34/20; A61B 5/283; A61B 5/287; A61B 5/6852; A61M 25/0136; A61M 25/0147
USPC ...................................................... 606/28–50
See application file for complete search history.

(56) References Cited

U.S. PATENT DOCUMENTS

| | | |
|---|---|---|
| 5,419,767 A | 5/1995 | Eggers et al. |
| 5,462,521 A | 10/1995 | Brucker et al. |
| 5,545,161 A | 8/1996 | Imran |
| 5,582,609 A | 12/1996 | Swanson et al. |
| 5,688,267 A | 11/1997 | Panescu et al. |
| 5,735,846 A | 4/1998 | Panescu et al. |
| 5,800,428 A | 9/1998 | Nelson et al. |
| 5,800,432 A | 9/1998 | Swanson |
| 5,904,651 A | 5/1999 | Swanson et al. |
| 5,947,988 A | 9/1999 | Smith |
| 5,964,757 A | 10/1999 | Ponzi |
| 6,110,196 A | 8/2000 | Edwards |
| 6,129,698 A | 10/2000 | Beck |
| 6,210,411 B1 | 4/2001 | Hofmann et al. |
| 6,217,576 B1 | 4/2001 | Tu et al. |
| 6,458,123 B1 | 10/2002 | Brucker et al. |
| 6,464,694 B1 | 10/2002 | Massengill |
| 6,576,858 B1 | 6/2003 | Yokomichi |
| 6,690,963 B2 | 2/2004 | Ben-Haim et al. |
| 7,104,989 B2 | 9/2006 | Skarda |
| 7,258,689 B2 | 8/2007 | Salvo |
| 7,549,989 B2 | 6/2009 | Morgan et al. |
| 7,815,635 B2 | 10/2010 | Wittkampf et al. |
| 7,901,403 B2 | 3/2011 | Woloszko et al. |
| 8,224,422 B2 | 7/2012 | Mottola et al. |
| 8,500,730 B2 | 8/2013 | Lee et al. |
| 9,510,894 B2 | 12/2016 | Clark et al. |
| 2001/0025179 A1 | 9/2001 | Levine |
| 2001/0051802 A1 | 12/2001 | Woloszko et al. |
| 2003/0009094 A1 | 1/2003 | Segner et al. |
| 2003/0163178 A1 | 8/2003 | Davison et al. |
| 2003/0212394 A1 | 11/2003 | Pearson et al. |
| 2004/0243157 A1 | 12/2004 | Connor et al. |
| 2005/0085769 A1 | 4/2005 | MacMahon et al. |
| 2006/0184165 A1 | 8/2006 | Webster, Jr. et al. |
| 2006/0241577 A1 | 10/2006 | Balbierz et al. |
| 2006/0264808 A1 | 11/2006 | Staid et al. |
| 2007/0156114 A1 | 7/2007 | Worley et al. |
| 2007/0156132 A1 | 7/2007 | Drysen |
| 2007/0270791 A1 | 11/2007 | Wang et al. |
| 2007/0287998 A1 | 12/2007 | Sharareh et al. |
| 2008/0161792 A1 | 7/2008 | Wang et al. |
| 2008/0255540 A1 | 10/2008 | Selkee |
| 2008/0287944 A1 | 11/2008 | Pearson et al. |
| 2009/0093810 A1 | 4/2009 | Subramaniam et al. |
| 2009/0093811 A1 | 4/2009 | Koblish et al. |
| 2009/0125016 A1 | 5/2009 | Wang et al. |
| 2009/0209949 A1 | 8/2009 | Ingle et al. |
| 2010/0030209 A1 | 2/2010 | Govari et al. |
| 2010/0069834 A1 | 3/2010 | Schultz |
| 2010/0168827 A1 | 7/2010 | Schultz |
| 2011/0264089 A1 | 10/2011 | Zirkle et al. |
| 2011/0270244 A1 | 11/2011 | Clark et al. |
| 2011/0270246 A1 | 11/2011 | Clark et al. |

FOREIGN PATENT DOCUMENTS

| | | |
|---|---|---|
| EP | 0 982 047 A2 | 3/2000 |
| EP | 1 690 510 A1 | 8/2006 |
| EP | 1 803 410 A1 | 7/2007 |
| EP | 2 145 596 A1 | 1/2010 |
| EP | 2 380 519 A1 | 10/2011 |
| JP | 2009-148550 A | 7/2009 |
| JP | 2010-505592 A | 2/2010 |
| WO | WO 96/34569 | 11/1996 |
| WO | WO 02/083228 A3 | 10/2002 |
| WO | WO 2011/008681 A1 | 1/2011 |

OTHER PUBLICATIONS

European Search Report dated Feb. 2, 2012 from EP Patent Application No. EP 12151275, 2 pages.
Extended European Search Report for corresponding Application No. EP 11163898.7-1269, dated Jul. 29, 2011, 6 pages.
Extended European Search Report for EP Application No. 14158294.0-1652, dated May 26, 2014, 7 pages.
English translation of JP Office Action dated Nov. 11, 2014 for Japanese Patent Application No. 2011-096838, 3 pgs.
State Intellectual Property Office of People's Republic China Search Report for Application No. 200910159385.5, dated Jul. 30, 2012, English language translation only, 2 pages.
English translation of CN Search Report dated May 23, 2014, issued in corresponding CN Application No. 201110118159, 3 pages.
European Examination Report dated Jul. 10, 2017, issued in corresponding EP Application No. 11163515.7, 5 pages.
Australian Patent Office Patent Examination Report No. 1 for AU Application No. 2015203554, dated Aug. 9, 2016, 3 pages.
European Patent Office Search Report for EP Application No. 11163515.7, dated Aug. 4, 2011, 6 pages.
English translation of SIPO Search Report dated May 14, 2017, issued in corresponding CN 201110116473.4, 3 pages.
EPO Search Report for EP Application No. 18179922.2 dated Jul. 25, 2018, 8 pages.

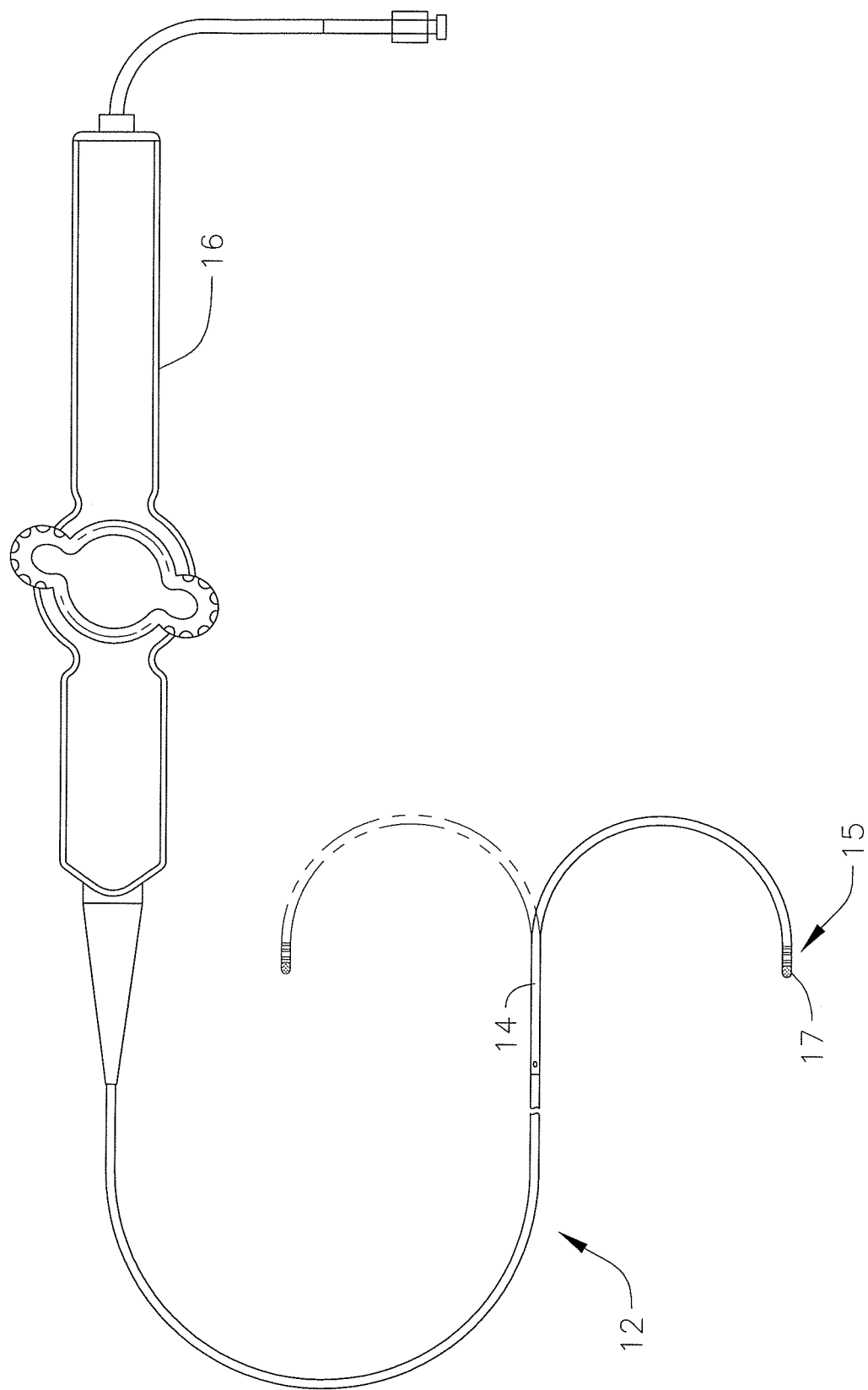

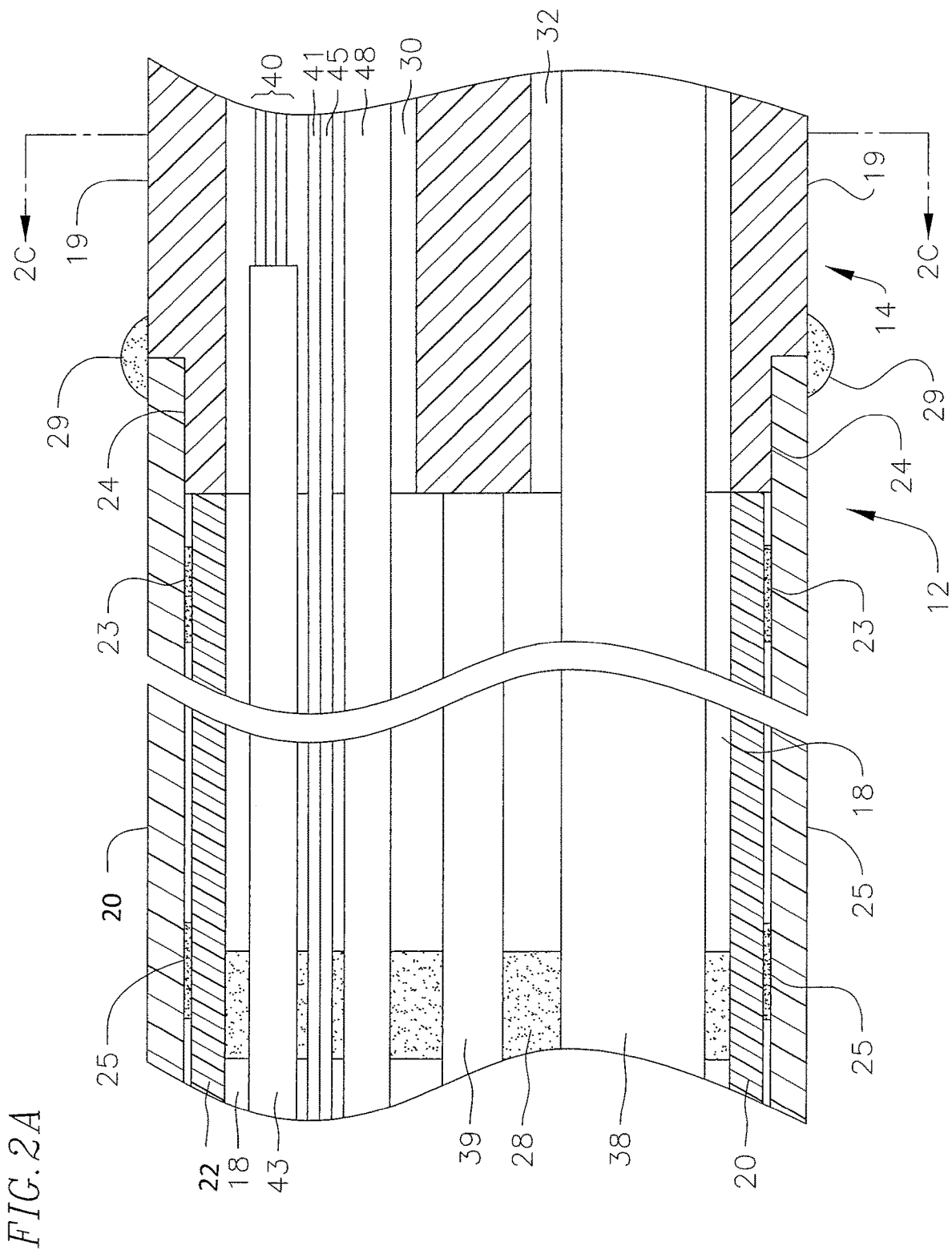

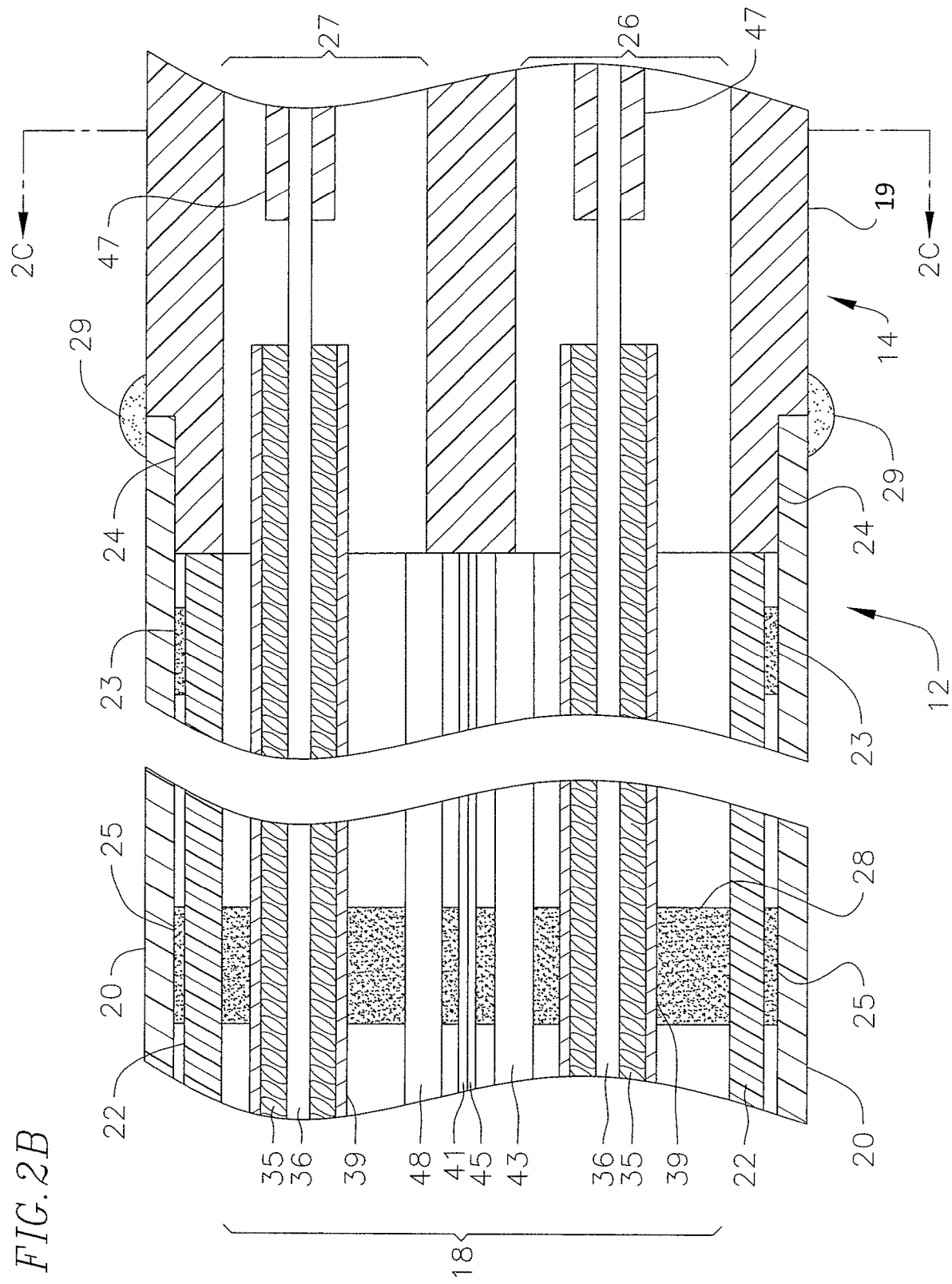

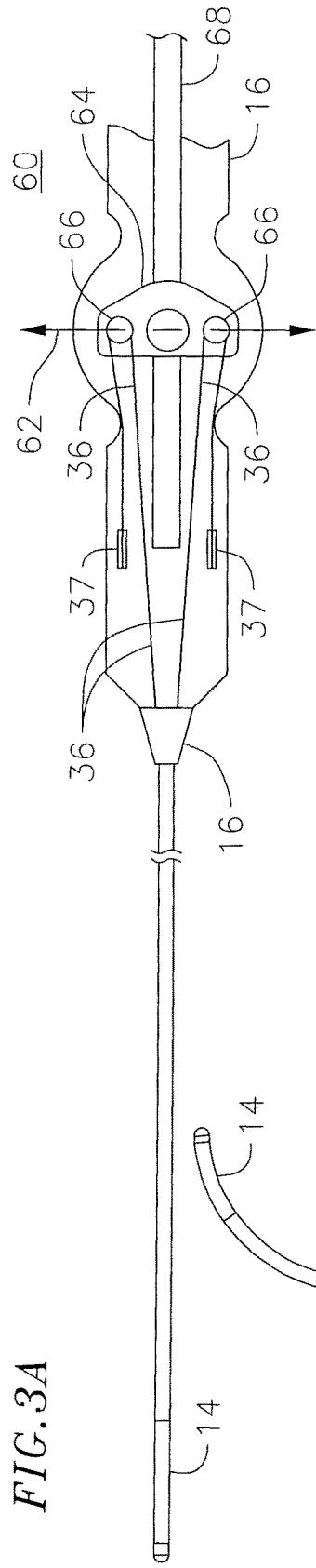
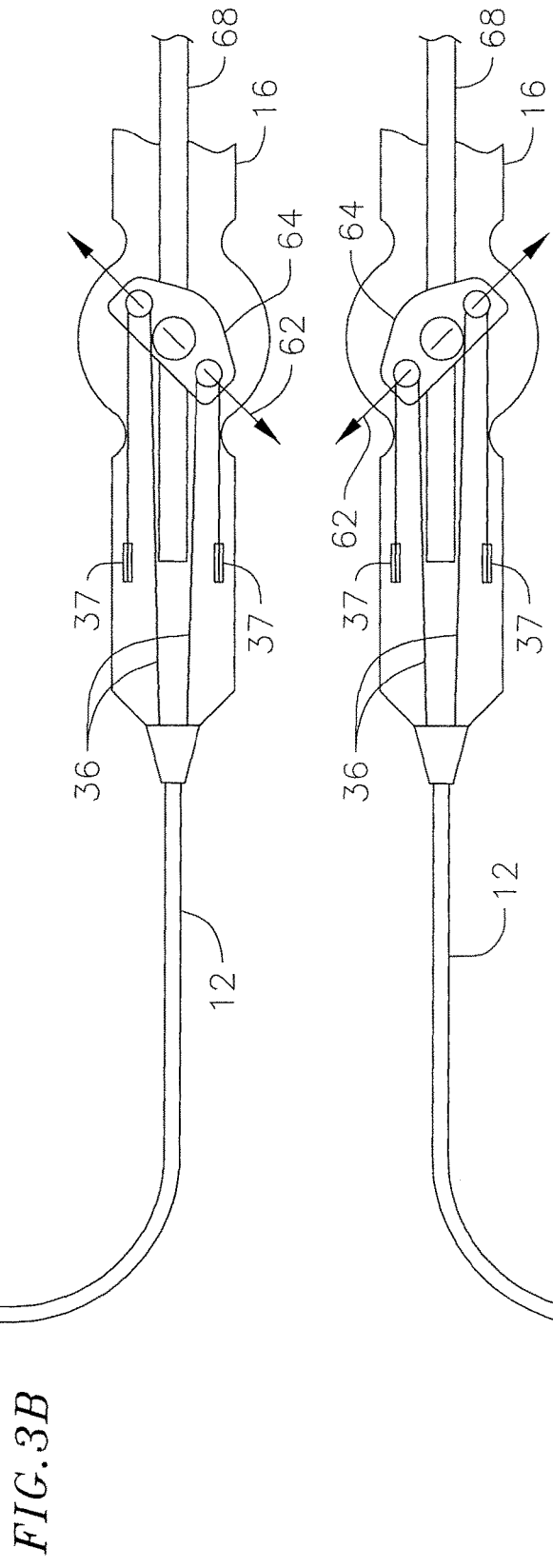
FIG.3A  FIG.3B  FIG.3C

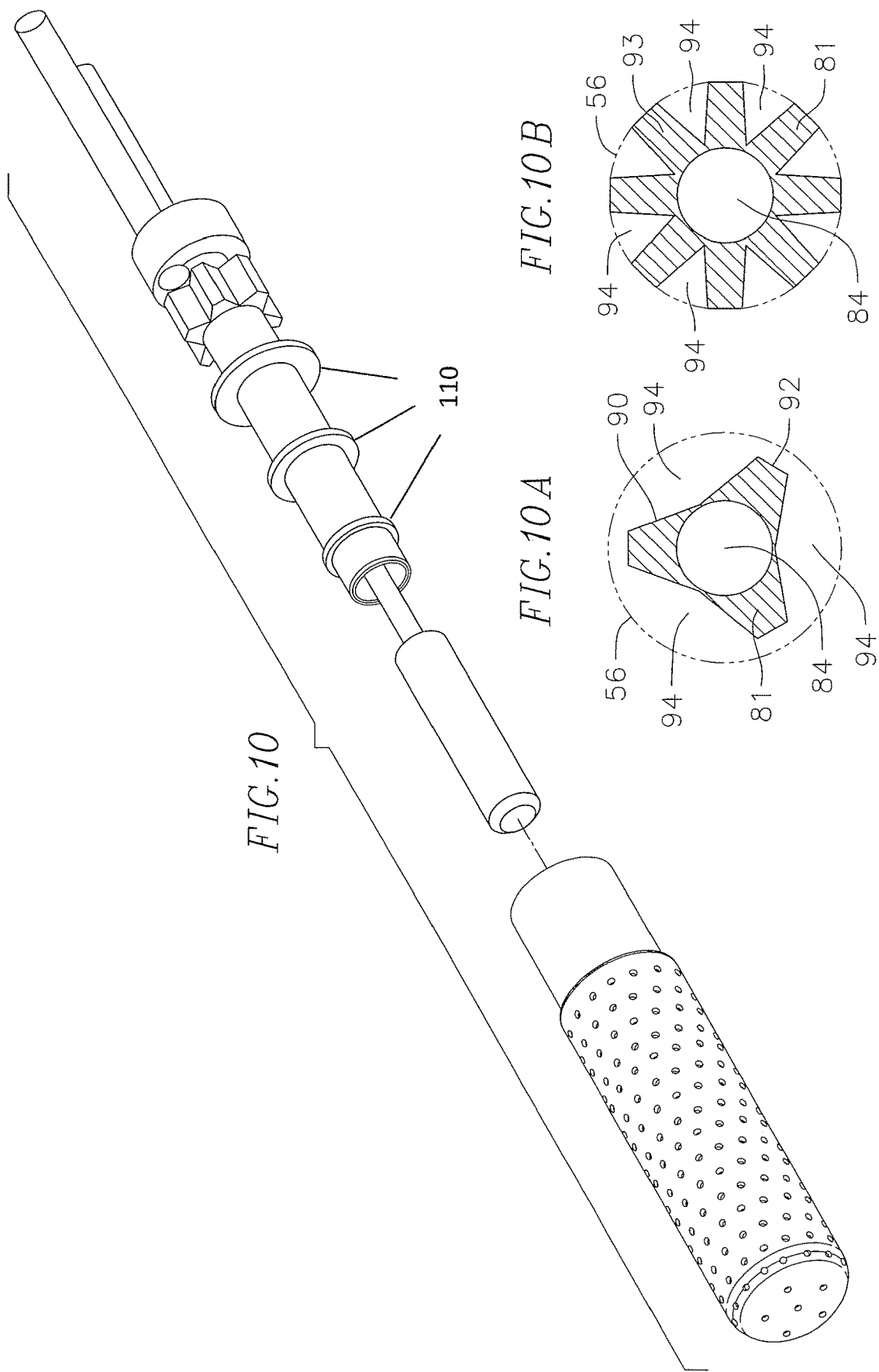

IRRIGATED CATHETER WITH INTERNAL POSITION SENSOR

CROSS-REFERENCE TO RELATED APPLICATION(S)

The present application is a continuation of and claims priority to and the benefit of U.S. patent application Ser. No. 15/960,402 filed Apr. 23, 2018, now issued as U.S. Pat. No. 10,265,124, which is a continuation of and claims priority to and the benefit of U.S. patent application Ser. No. 12/767,763 filed Apr. 26, 2010, now issued as U.S. Pat. No. 9,949,791, the entire contents of all of which are incorporated herein by reference.

FIELD OF INVENTION

The present invention relates to an electrophysiologic catheter that is particularly useful for ablation and sensing electrical activity of heart tissue.

BACKGROUND OF INVENTION

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the tissue target areas at which ablation is to be performed.

In use, the electrode catheter is inserted into a major vein or artery, e.g., the femoral artery, and then guided into the chamber of the heart which is of concern. A reference electrode is provided, generally taped to the patient's skin. Radio frequency (RF) current is applied to the tip electrode, and flows through the surrounding media, i.e., blood and tissue, toward the reference electrode. The distribution of current depends on the amount of electrode surface in contact with the tissue, as compared to blood which has a higher conductivity than the tissue.

Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than tissue, impedance to the flow of electrical energy into the tissue also increases. If the impedance increases sufficiently, an impedance rise occurs and the catheter must be removed from the body and the tip electrode cleaned.

In a typical application of RF current, circulating blood provides some cooling of the ablation electrode. Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

Another consideration is the ability to control the exact position and orientation of the catheter tip. This is ability is critical and largely determines the usefulness of the catheter. It is generally known to incorporate into electrophysiology catheters an electromagnetic (EM) tri-axis location/position sensor for determining the location of a catheter's distal end. An EM sensor in the catheter, typically near the catheter's distal end within the distal tip, gives rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

U.S. Pat. No. 5,391,199, the entire disclosure of which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional coordinates of the coil.

U.S. Pat. No. 6,690,963, the entire disclosure of which is hereby incorporated by reference, is directed to a locating system for determining the location and orientation of an invasive medical instrument, for example a catheter or endoscope, relative to a reference frame, comprising: a plurality of field generators which generate known, distinguishable fields, preferably continuous AC magnetic fields, in response to drive signals; a plurality of sensors situated in the invasive medical instrument proximate the distal end thereof which generate sensor signals in response to said fields; and a signal processor which has an input for a plurality of signals corresponding to said drive signals and said sensor signals and which produces the three location coordinates and three orientation coordinates of a point on the invasive medical instrument.

Because of the size of the tip electrode and the limited interior space therein, the EM sensor is often positioned outside of the tip electrode, proximally thereof, and often off axis from the tip electrode which can reduce the accuracy of the position sensing capabilities of the sensor. Being outside the tip electrode, the position sensor is also exposed to bending stresses and can limit the flexibility and deflection of the distal tip section. Moreover, the sensor can be damaged by RF energy during ablation.

Where the distal tip is irrigated, the efficiency of irrigated cooling becomes a significant factor as ablation procedures can last five or six hours resulting in extensive fluid-loading in the patient. Conventional irrigated tip electrodes typically operate with a flow rate of about 17 ml/minute at below about 30 watts of RF ablation energy to about 30-50 ml/minute at about 30 watts or greater. The limited space in the distal tip may also lead to anchoring of the puller wires to a less desirable location such as a tubing wall causing tearing of the tubing wall and/or unintended asymmetrical deflection.

Accordingly, it is desirable that a catheter be adapted for mapping and ablation with improved cooling and position sensing characteristics by providing a tip configuration that includes housing in which the position sensor is protected and is located both distally and on-axis without inhibiting the flow and dispersion of irrigation fluid through the tip. It is also desirable that such a catheter exhibit symmetrical bi-directional deflection and that the walls of the catheter be damaged from deflection puller wires.

SUMMARY OF THE INVENTION

The present invention is directed to a catheter adapted for mapping and ablating heart tissue that carries a position sensor in a distal, on-axis position in an irrigated ablation tip electrode. The catheter of the present invention has an elongated catheter body and a deflectable section distal the catheter body. The tip electrode has an internal configuration that promotes fluid diffusion and dispersion.

In one embodiment, the tip electrode has a shell wall that defines a cavity through which fluid flows and exits via fluid ports formed in the shell wall. The cavity is sealed by an internal member extends into the cavity with a baffle portion and a distal portion. The distal portion safely houses the position sensor and the baffle portion diffuses and disperses fluid entering the tip electrode for a more uniform flow through the cavity. The distal portion is configured to provide an annular region that runs along the length of the tip electrode to better feed fluid to the more distal fluid ports on the tip electrode for more uniform cooling at all locations on the tip electrode.

In a more detailed embodiment, the baffle portion has a cross-section nonconforming to an inner space of the shell so that separate and distinct axial flow paths are provided to slow axial momentum of the fluid entering the tip electrode. For example, where the inner space of the shell is generally circular, the baffle portion has a polygonal (regular or irregular) cross-section upon which fluid impinges when entering the cavity of the tip electrode. Additionally, the passage by which fluid enters the cavity has an elongated cross-section for more efficient use of space inside the tip electrode.

BRIEF DESCRIPTION OF THE DRAWINGS

These and other features and advantages of the present invention will be better understood by reference to the following detailed description when considered in conjunction with the accompanying drawings wherein:

FIG. 1 is a side view of an embodiment of a catheter of the present invention.

FIG. 2A is a side cross-sectional view of the catheter FIG. 1, showing a junction between a catheter body and a deflectable intermediate section, taken along a first diameter.

FIG. 2B is a side cross-sectional view of the catheter of FIG. 1, showing a junction between a catheter body and a deflectable intermediate section, taken a long a second diameter generally perpendicular to the first diameter.

FIGS. 3A-3C are schematic diagrams of an embodiment of a control handle showing the catheter in the neutral and deflected positions.

FIG. 10 is an exploded perspective view of an alternate embodiment of a tip electrode assembly.

FIG. 10A is an end cross-sectional view of an alternate embodiment of an internal member.

FIG. 10B is an end cross-sectional view of another alternate embodiment of an internal member.

DETAILED DESCRIPTION OF THE INVENTION

Figure 2C:
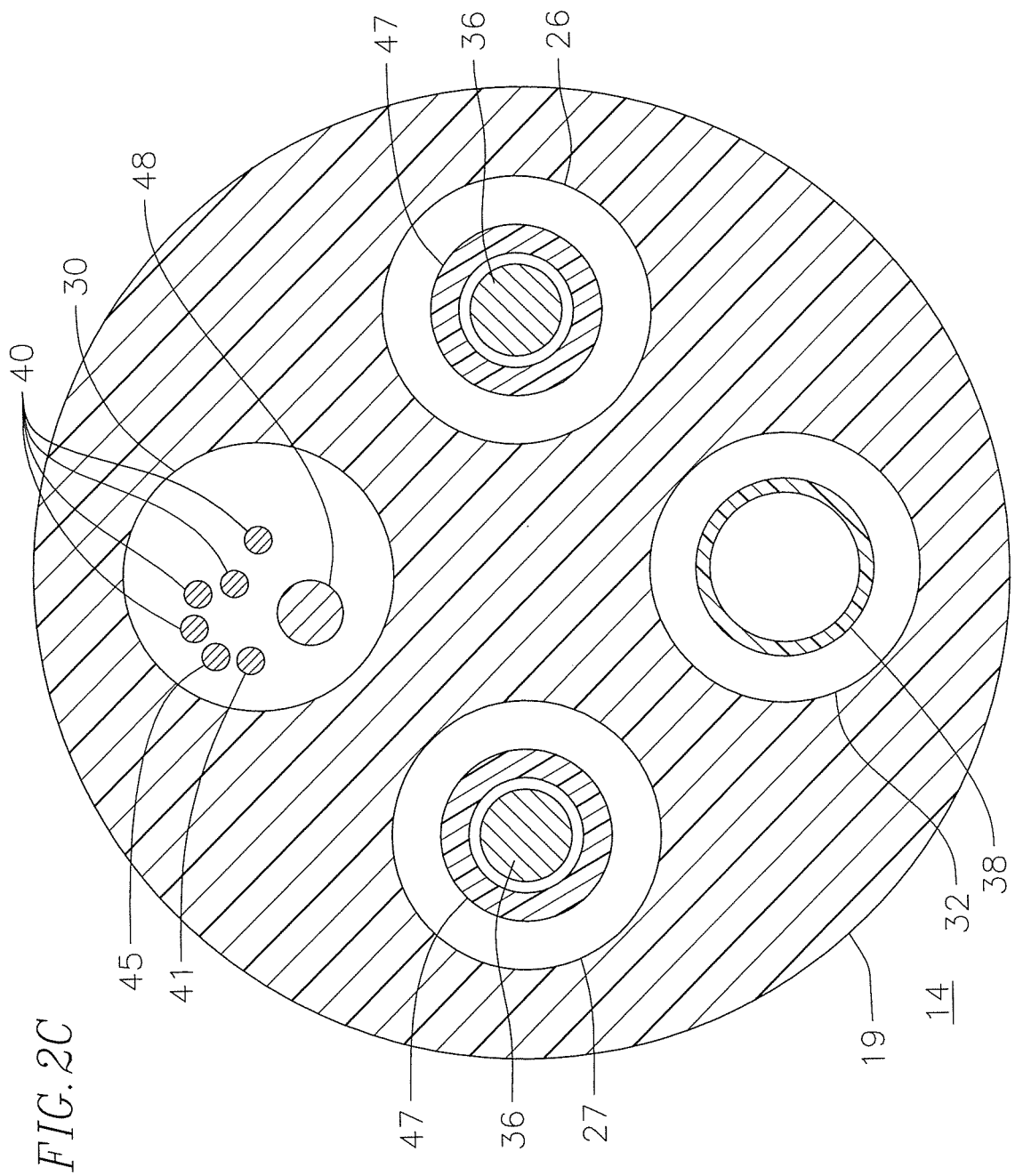
FIG. 2C is a longitudinal cross-section view of the deflectable intermediate section of FIGS. 2A and 2B taken along line c-c.

FIG. 1 illustrates an embodiment of a catheter 10 with improved position sensing and cooling capabilities. The catheter has an elongated catheter body 12 with proximal and distal ends, an intermediate deflectable section 14 at the distal end of the catheter body 12, and a distal section 15 with an irrigated mapping and ablation tip electrode 17. The catheter also includes a control handle 16 at the proximal end of the catheter body 12 for controlling bi-directional deflection of the intermediate section 14. Advantageously, the tip electrode 17 houses an electromagnetic position sensor in a distal and on-axis location while shielding the sensor from RF ablation and bending stresses. The tip electrode is also configured to promote turbulent flow and dispersion of irrigation fluid for increased thermal transfer from the shell to the fluid and thus with lower flow rates resulting in lower fluid load in the patient. Fluid, e.g., saline or heparinized saline, can be delivered to the ablation site from the tip electrode to cool tissue, reduce coagulation and/or facilitate the formation of deeper lesions. It is understood that other fluids can be delivered as well, including any diagnostic and therapeutic fluids, such as neuroinhibitors and neuroexcitors.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.'

Distal ends of the stiffening tube 22 and the outer wall 20 are fixedly attached near the distal end of the catheter body 12 by forming a glue joint 23 with polyurethane glue or the like. A second glue joint 25 is formed between proximal ends of the stiffening tube 22 and outer wall 20 using a slower drying but stronger glue, e.g., polyurethane.

Components that extend between the control handle 16 and the deflectable section 14 pass through the central lumen 18 of the catheter body 12. These components include lead wires 40 for the tip electrode 17 and ring electrodes 21 on the tip section, an irrigation tubing 38 for delivering fluid to the tip section 15, a cable 48 for the position location sensor 46, a pair of puller wires for deflecting the intermediate section 14, and a pair of thermocouple wires 41, 45 to sense temperature at the distal tip section 15. Glue joint 28 affixes the proximal portion of the components inside the stiffening tube.

Illustrated in FIGS. 2A, 2B and 2C is an embodiment of the intermediate section 14 which comprises a short section of tubing 19. The tubing also has a braided mesh construction but with multiple off-axis lumens, for example lumens 26, 27, 30 and 32. Each of diametrically opposing first and second lumens 26 carries a puller wire 36 for bi-directional deflection. A third lumen 30 carries the lead wires 40, the thermocouple wires 41 and 45, and the sensor cable 48. A fourth lumen 32 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 24 that receives an inner surface of the outer wall 20 of the catheter body 12. The intermediate section 14 and catheter body 12 are attached by glue 29 or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 36 is preferably coated with Teflon®. The puller wires 36 can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, a portion of each puller wire 36 extending through the catheter body 12 passes through a compression coil 35 in surrounding relation to its puller wire 36. The compression coil 35 extends from the proximal end of the catheter body 12 to the proximal end of the intermediate section 14. The compression coil 35 is made of any suitable metal, preferably stainless steel, and is tightly wound on itself to provide flexibility, i.e., bending, but to resist compression. The inner diameter of the compression coil is preferably slightly larger than the diameter of the puller wire 36. Within the catheter body 12, the outer surface of the compression coil 35 is also covered by a flexible, non-conductive sheath 39, e.g., made of polyimide tubing. As shown in FIGS. 2B and 2C, a portion of each puller wire 36 extending through the intermediate section 14 is covered by a nonconductive protective sheath 47.

Proximal ends of the puller wires 36 are anchored in the control handle 16. Distal ends of the puller wires 36 are anchored in the tip section 15 as described further below. Separate and independent longitudinal movement of the puller wire 36 relative to the catheter body 12 which results in deflection of the intermediate section 14 and tip section 15 is accomplished by suitable manipulation of the control handle 16.

Figure 4:
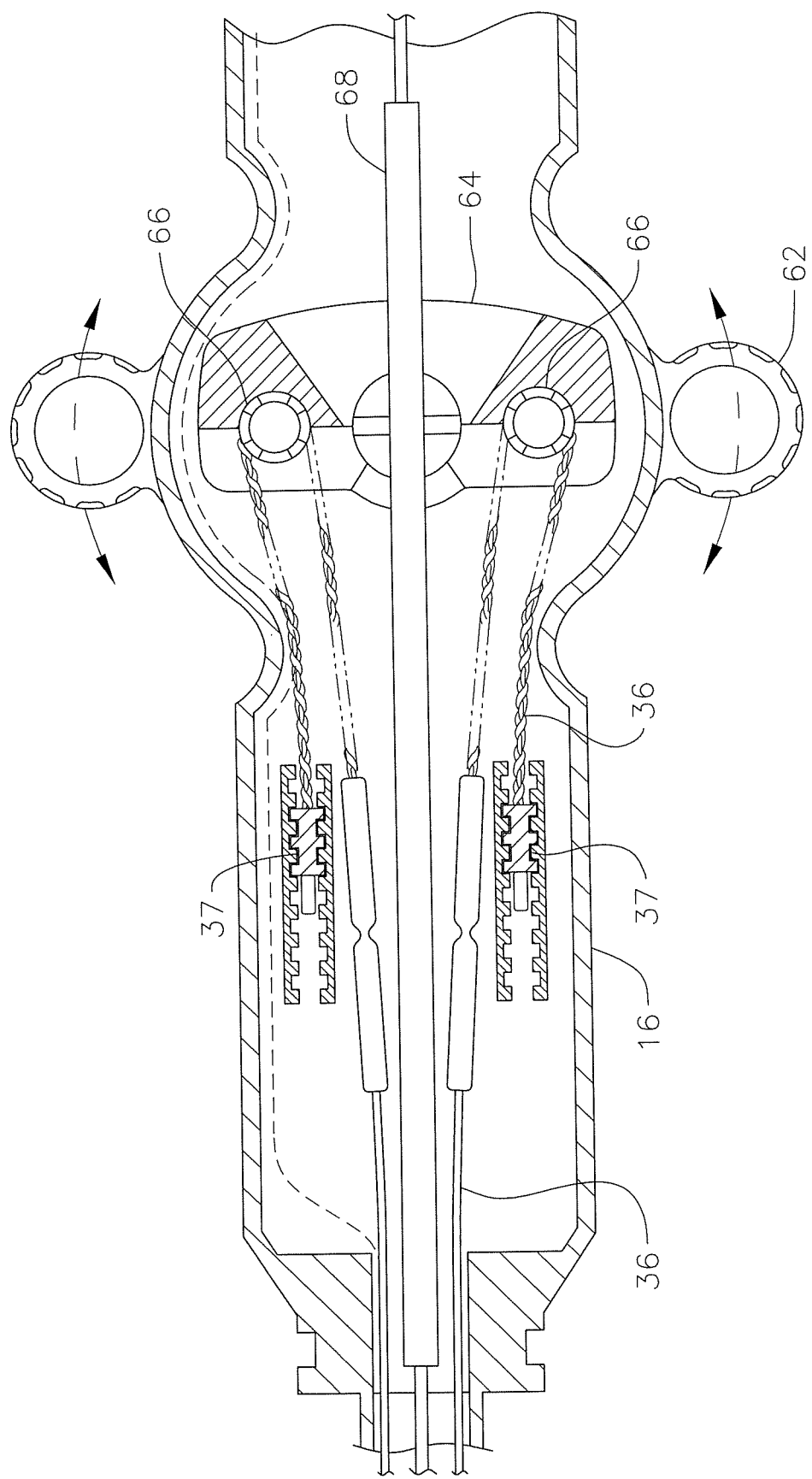
FIG. 4 is a top plan view of an embodiment of a control handle, including a deflection control assembly.
Figure 5:
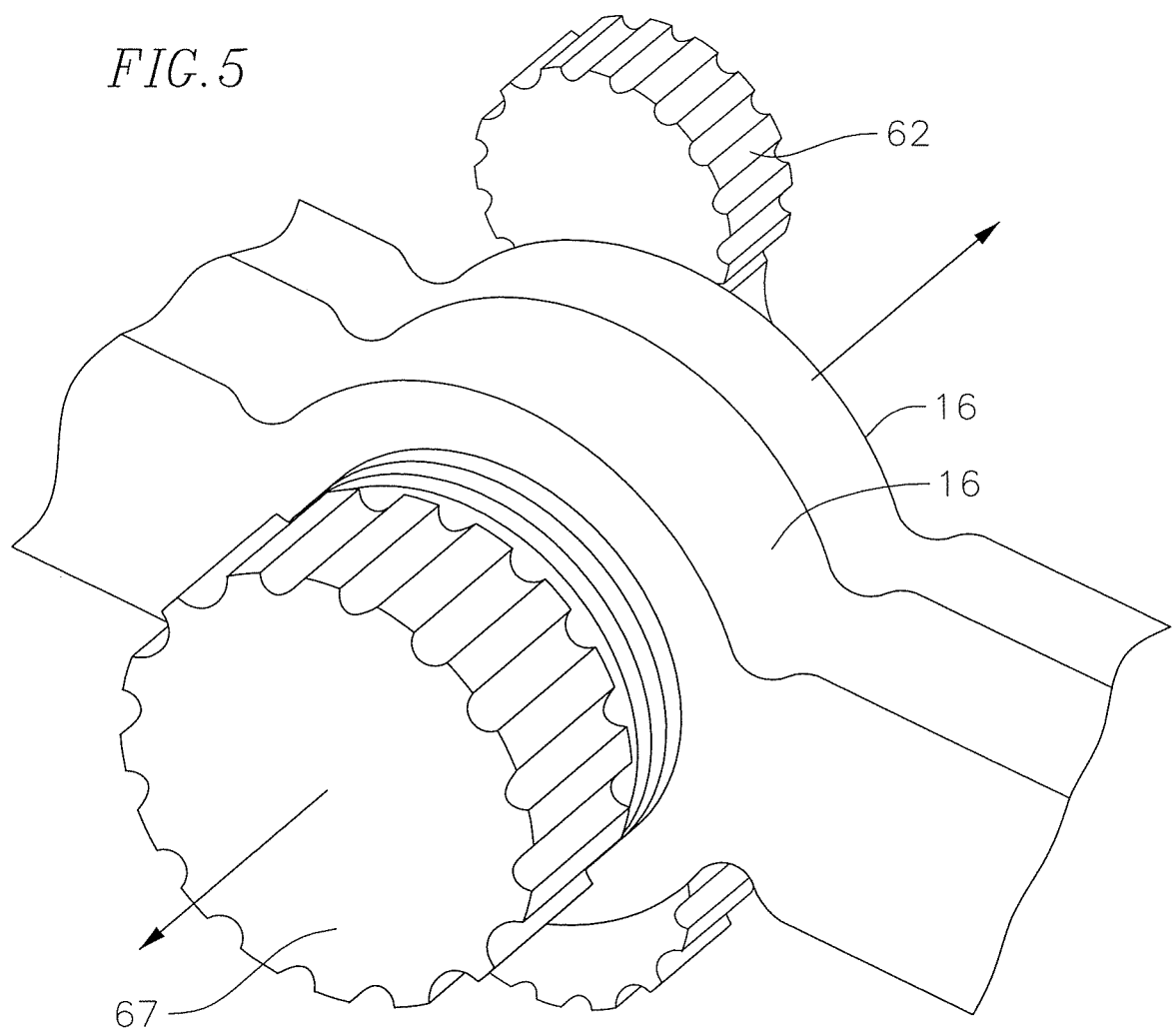
FIG. 5 is a partial side perspective view of an embodiment of a deflection arm and a tension adjustment knob as mounted on a control handle.
Figure 7:
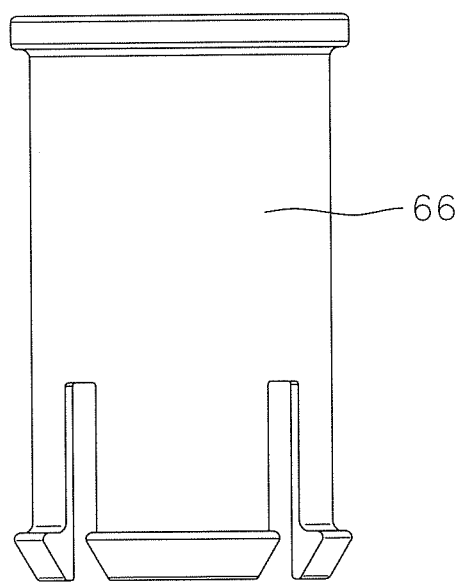
FIG. 7 is a side elevational view of an embodiment of a pulley as used in a deflection control assembly.
Figure 6B:
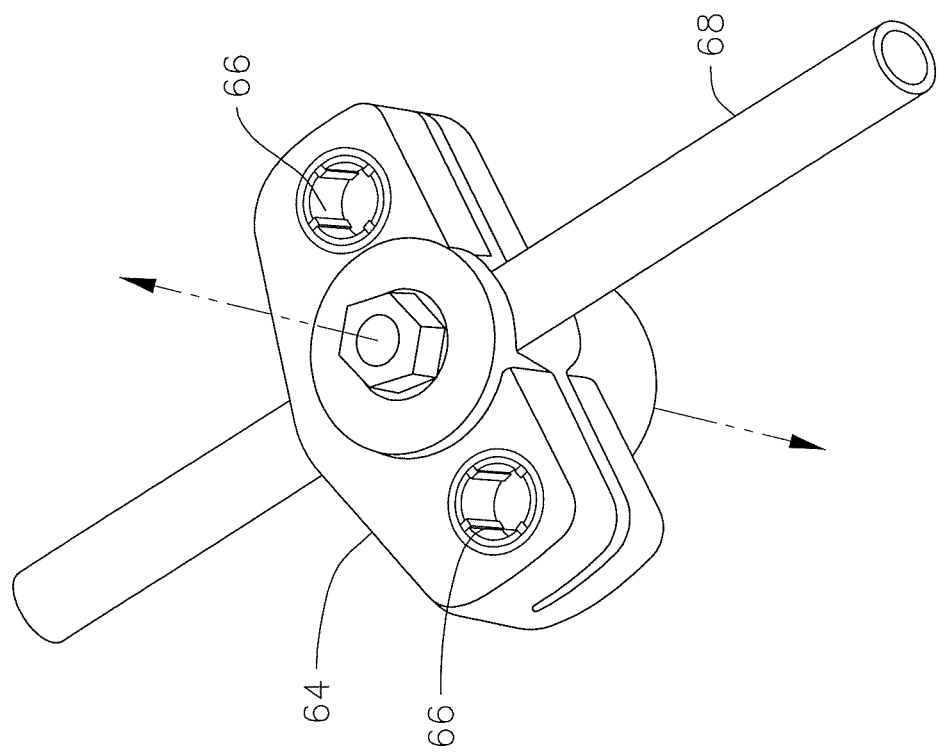
FIGS. 6A and 6B are perspective top and bottom views of an embodiment of a rocker member as used in a deflection control assembly.
Figure 6A:
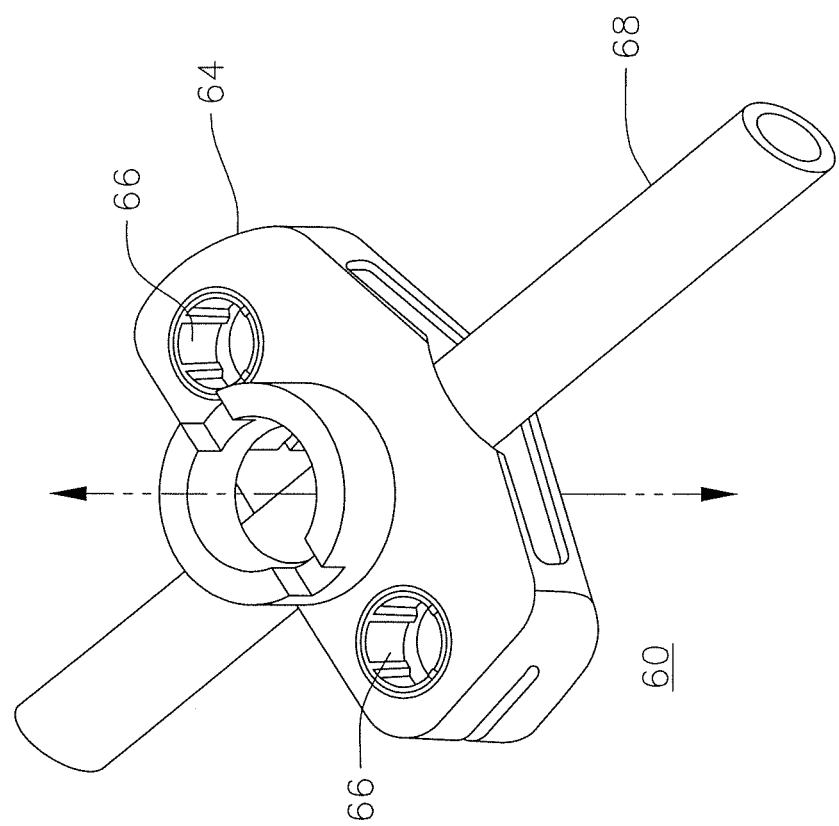

In the illustrated embodiment, the control handle 16 has a deflection assembly 60 (FIG. 4) with a deflection arm 62 (FIG. 5), and a rotatable or rocker member 64 (FIGS. 6A and 6B) supporting a pair of pulleys 66 (FIG. 7) that act on the puller wires 36 to deflect the intermediate section 14 and thus the tip section 15. The deflection arm 62 and the rocker member 64 are rotationally aligned and coupled such that rotation of the deflection arm 62 by a user rotates the rocker member 64. As the rocker member 64 is rotated by means of the deflection arm (represented by line 62), the pulleys 66 are displaced from a neutral position (FIG. 3A) with one pulley 66 drawing a puller wire 36 on one side of the catheter against its anchored proximal end 37 for deflecting the section 14 toward that side (FIGS. 3B and 3C). Components such as the lead wires, irrigating tubing and sensor cable can extend through the rocker member 64 within a protective tubing 68. A deflection tension knob 67 (FIG. 5) enables the user to adjust the ease by which the deflection arm 62 can be rotated. A suitable deflection assembly and control handle are described in co-pending U.S. application Ser. No. 12/346,834, filed Dec. 30, 2008, entitled DEFLECTABLE SHEATH INTRODUCER, the entire disclosure of which is hereby incorporated by reference. Other suitable deflection assemblies are described in co-pending U.S. application Ser. No. 12/211,728, filed Sep. 16, 2008, entitled CATHETER WITH ADJUSTABLE DEFLECTION SENSITIVITY, and U.S. application Ser. No. 12/127,704, filed May 27, 2008, entitled STEERING MECHANISM FOR BI-DIRECTIONAL CATHETER, the entire disclosures of both of which are hereby incorporated by reference.

Figure 8:
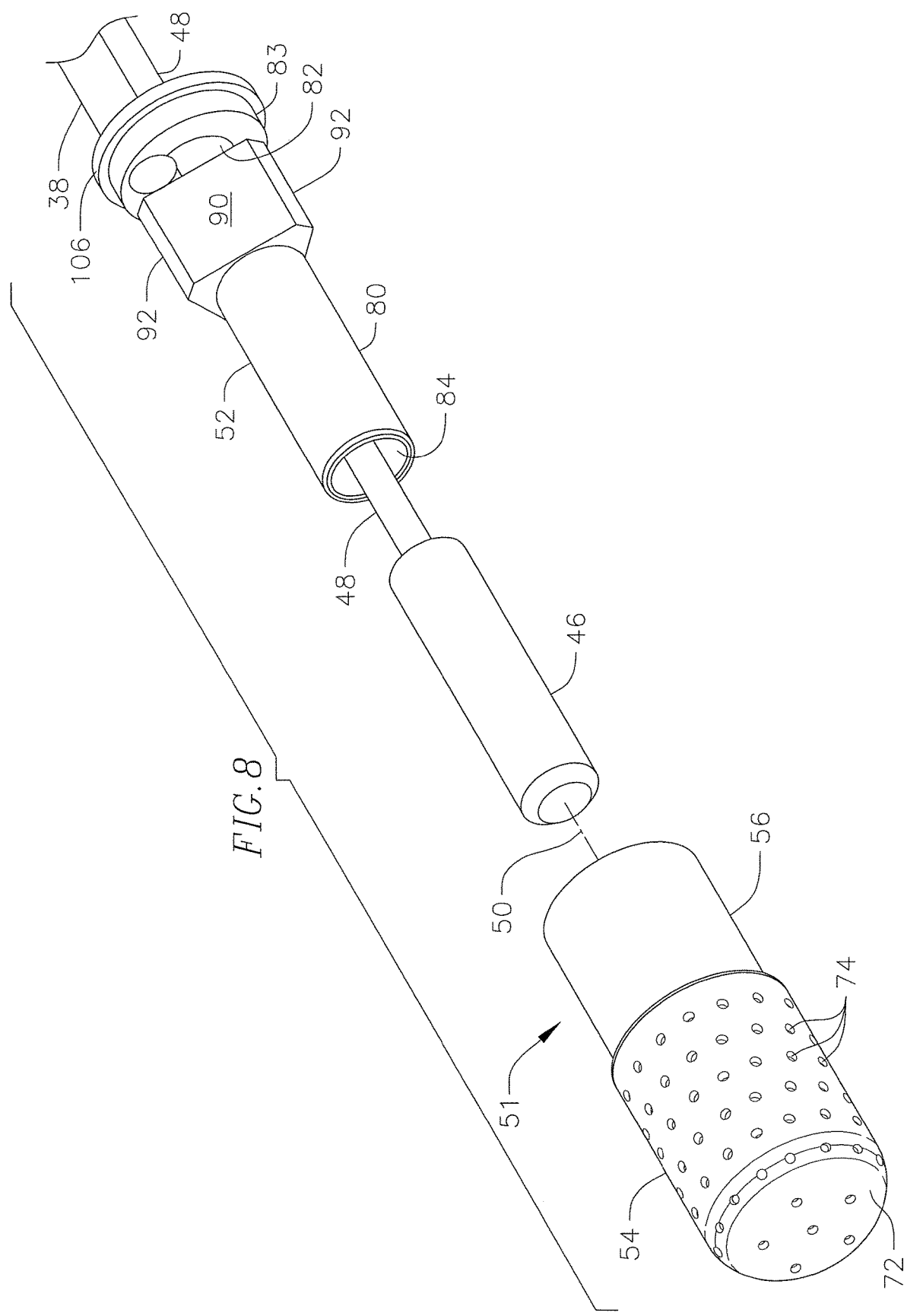
FIG. 8 is an exploded perspective view of an embodiment of a tip electrode assembly.
Figure 9:
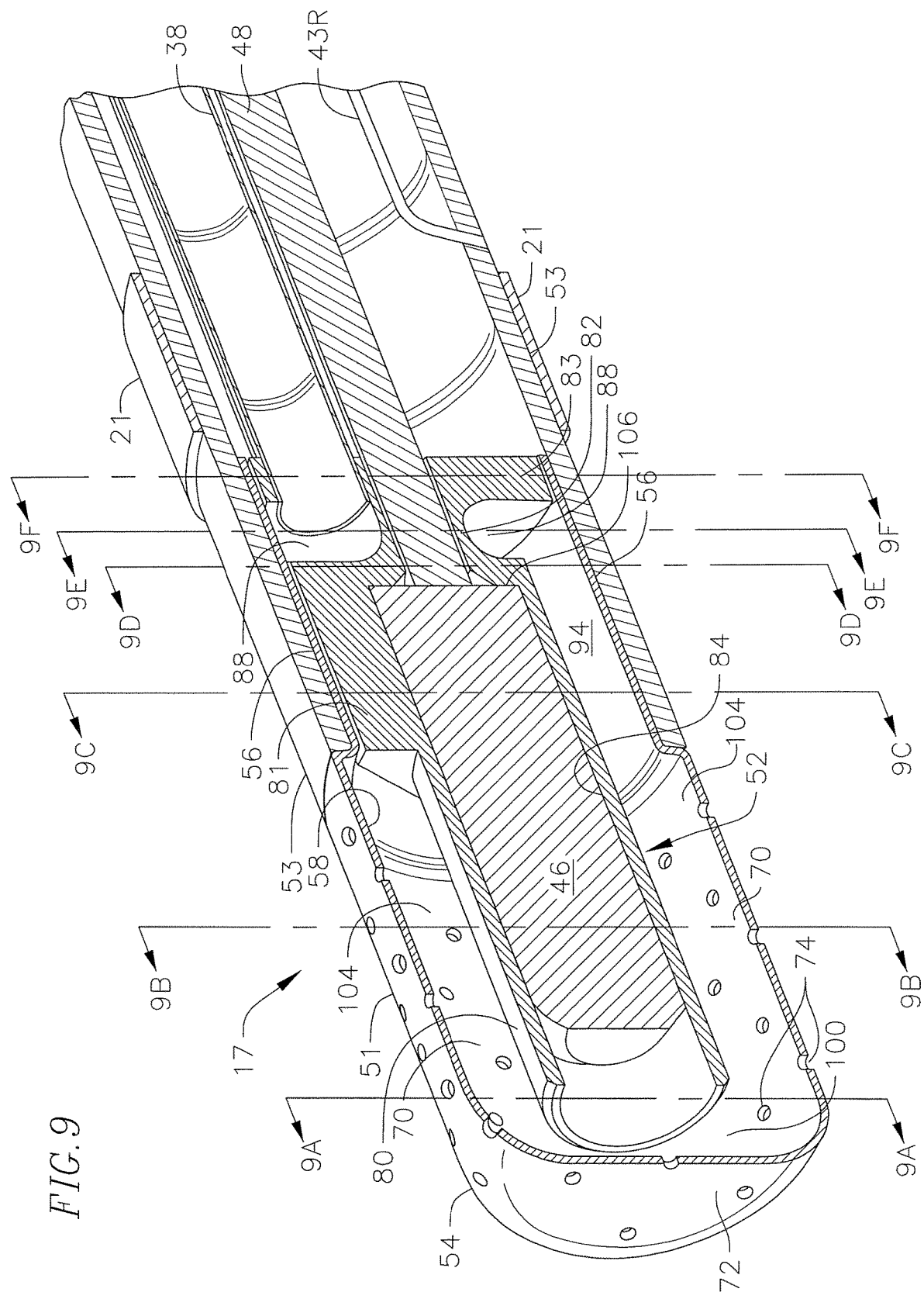
FIG. 9 is a cross sectional perspective view of an embodiment of a tip electrode assembly.

At the distal end of the intermediate section 14 is the tip section 15 that includes the tip electrode 17 and a relatively short piece of connector tubing 53 between the tip electrode 17 and the intermediate section 14. In the illustrated embodiment of FIGS. 8 and 9, three ring electrodes 21 are mounted on the tubing 53 and the tubing 53 has a single lumen which allows passage of the tip electrode lead wire 40T, the electromagnetic sensor cable 48, thermocouple wires 41 and 45, and the irrigation tubing 38 into the tip electrode 17. The single lumen of the connector tubing 53 allows these components to reorient themselves as needed from their respective lumens in the intermediate section 14 toward their location within the tip electrode 17.

The tip electrode 17 defines a longitudinal axis 50 and is of a two piece configuration that includes an electrically conductive shell or dome 51 and internal member or housing 52. The shell is generally cylindrical configuration. It has a narrower open neck portion 56 that is proximal of a wider distal portion 54. The distal portion has an atraumatic distal end 72 with a flat distal surface and a rounded circumferential edge. The distal portion has an inner wall 58 that defines a generally cylindrical cavity 70 within the shell. The proximal neck portion 56 is aligned and on axis with the longitudinal axis 50. It is understood that the neck portion 56 need not be narrower than the distal portion 54. Indeed, the two portions may have the same diameter, except the distal portion 54 is exposed whereas the neck portion 56 is covered by the connector tubing 43.

The shell 51 is constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell is constructed of an alloy comprising about 90% platinum and about 10% iridium by weight. The shell 51 can formed by deep-drawing manufacturing process which produces a sufficiently thin but sturdy wall that is suitable for handling, transport through the patient's body, and tissue contact during mapping and ablation procedures. A deep drawn shell is also suitable for electrical discharge machining (EDM) process to form a large plurality of through-holes or ports 74 in the distal portion 54 that allow communication between the cavity 70 and outside the shell 51. In a disclosed embodiment, the shell has a wall thickness ranging between about 0.002" and 0.005", preferably between about 0.003" and 0.004", and the wall has a plurality of holes ranging between about 21 and 140, preferably between about 33 and 60, more preferably between about 33 and 57, where a diameter of each hole can range between about 0.002" and 0.010", preferably between about 0.003" and 0.004", and preferably about 0.004 inch in diameter.

The internal member 52 is configured to protect and encapsulate the sensor 46 in a distal and centered location within the cavity 70 so that the sensor is distal and centered in the tip electrode for optimum performance. That is, the more centered the sensor is in the tip electrode and the closer the sensor is to the distal end of the tip electrode, the more accurate is the data provided by the sensor. In the illustrated embodiment, the entirety of the internal member 52 is received in the shell 51.

The internal member 52 has an elongated configuration that is aligned and on-axis with the longitudinal axis 50 of the tip section 15. Advantageously, the internal member has a tubular distal portion 80, a baffle mid-portion 81, a stem portion 82, and a proximal base portion 83. Extending through the entire length of the internal member is an on-axis passage 84 to receive the sensor 46 and the sensor cable 48. In a disclosed embodiment, the tubular distal portion 80 is situated generally in the cavity 70 of the shell, and the baffle, stem and base portions 81, 82, 83 are situated generally in the neck portion 56 of the shell. That is, the two piece configuration allows the internal member 52 to be inserted and received in shell 51, where the tubular distal portion 80 extends in the distal portion 54 of the shell 51, and the proximal remainder (the baffle mid-portion 81, the stem portion 82 and the base portion 83) extends in the neck portion 56 of the shell 51.

Figure 9A:
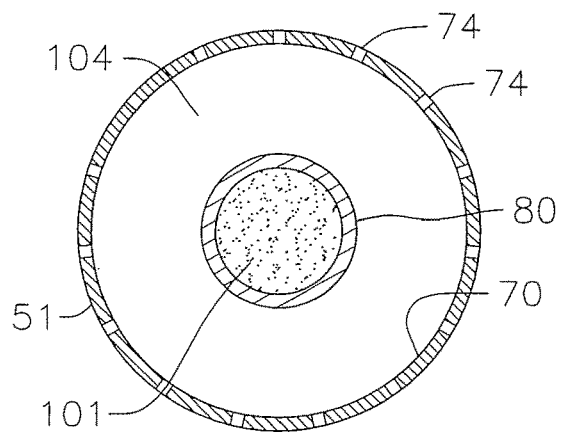
FIG. 9A is a longitudinal cross sectional view of the tip electrode assembly of FIG. 9, taken along line a-a
Figure 9B:
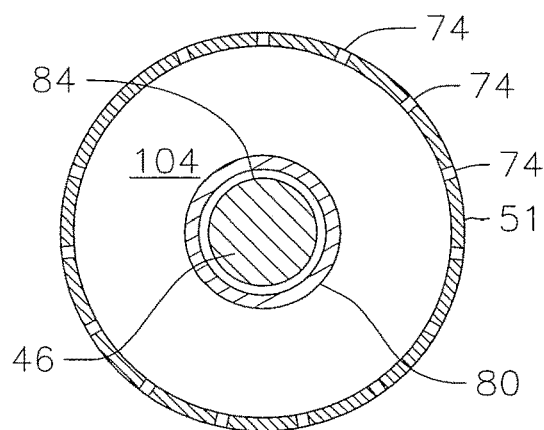
FIG. 9B is a longitudinal cross sectional view of the tip electrode assembly of FIG. 9, taken along line b-b
Figure 9C:
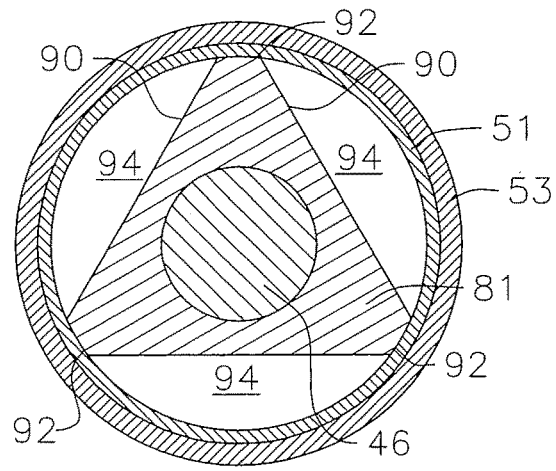
FIG. 9C is a longitudinal cross sectional view of the tip electrode assembly of FIG. 9, taken along line c-c

The base portion 83 of the internal member 52 has a circular cross section (FIG. 9f) that is adapted for a snug fit with the neck portion 56 of the shell to form a fluid-tight seal at the proximal end of the tip electrode 17. The base portion can have a thickness ranging between about 0.003" to 0.004".

Figure 9E:
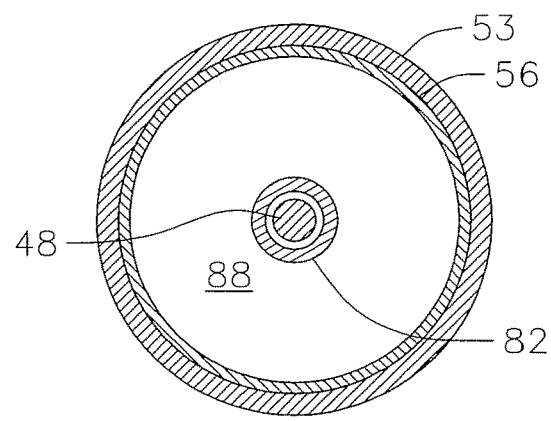
FIG. 9E is a longitudinal cross sectional view of the tip electrode assembly of FIG. 9, taken along line e-e

Distal the base portion is the narrowed stem portion 82 which creates an open annular gap 88 within the shell 51 between the base portion 83 and the baffle mid-portion 81 (FIG. 9e). The width of the stem portion can range between about 0.090" to 0.110".

Figure 9D:
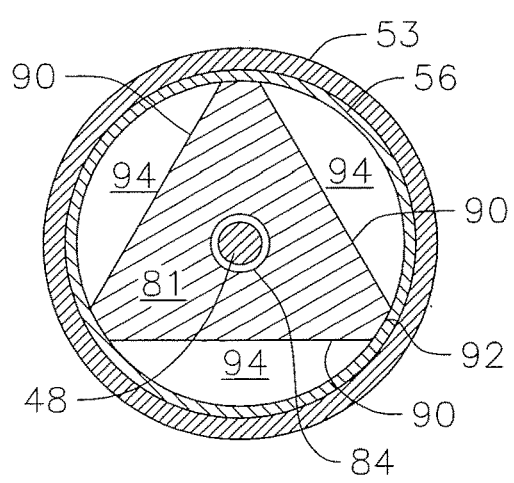
FIG. 9D is a longitudinal cross sectional view of the tip electrode assembly of FIG. 9, taken along line d-d
Figure 9F:
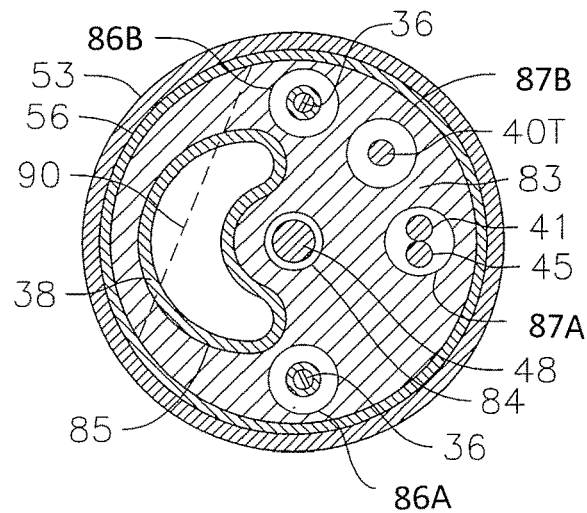
FIG. 9F is a longitudinal cross sectional view of the tip electrode assembly of FIG. 9, taken along line f-f

The illustrated embodiment of the baffle mid-portion 81 includes an equilateral triangular cross-section (FIG. 9d) with three edges 90 spanning between three truncated corners 92 that are in circumferential contact with the neck portion 56 of the shell 51. This contact advantageously enables a snug and on-axis (or centered) fit between the shell 51 and the internal member 52. The triangular cross-section also advantageously creates different axial flow paths or channels 94 for fluid passing into the tip electrode 17. The fluid flowing into the cavity 70 of the shell 51 is separated into distinct flow paths by the baffle mid-portion 81. These flow paths facilitate dispersion of fluid entering the tip electrode 14 at the base portion. It is understood that the cross-section of the baffle portion 81 need not be limited to a triangular configuration, but could be polygonal, including quadrilateral or pentagonal, so long as multiple flow paths are formed and turbulence is generated without significant drop in fluid pressure. The length of the baffle portion between its distal and proximal end can range between about 0.050" to 0.200".

The tubular portion 80 has a length and an inner diameter so that it can receive the sensor 46 in its entirety and leave a gap 100 between the distal end of the tubular portion and a distal end of the sensor. A conventional sensor has a diameter about 1 mm and a length about 5 mm. The gap 100 is filled by a sealant 101 (FIG. 9A), such as polyurethane, so that the sensor is effectively fixed, sealed and protected in the tubular portion 80. The tubular portion has a length that ranges between about 60% to 90% of the length of the cavity, and preferably about 80%. In an alternate embodiment, the tubular portion is a separate component from the baffle portion and is sealed to the latter. The baffle portion, 81, must be made of electrically conductive material, but the tubular portion can be made of plastic such as polyimide. The tubular portion has an outer diameter that ranges between about 25% and 40% of the diameter of the cavity 70, and preferably about 30% (FIGS. 9B and 9C). These differences in length and diameter advantageously leave a distal gap 102 between a distal end of the shell 51 and a distal end of the tubular portion 80, and an annular region 104 spanning at least the length of the tubular portion for improved fluid dispersion and flow in the tip electrode. In the illustrated embodiment, the tubular portion 80 has a circular cross-section, although it is understood that the cross-section can be any appropriate shape, including any polygonal configuration, e.g., triangular, rectangular, etc.).

At the proximal end of the sensor 46, the passage 84 through the internal member 52 narrows to form a stop 106 (FIG. 9C) to abut against the proximal end of the sensor 46. A junction of the sensor and the sensor cable lies at the stop and the sensor cable extends proximally therefrom through the reminder of the passage 84 and into the intermediate section 14. The junction between the cable 48 and the sensor 46 is thus hidden inside the internal member 52, surrounded by the internal member and better protected against cable detachment and bending stresses. This feature also enables an overall shorter length in the tip electrode allowing for a more maneuverable catheter.

Other formations in the base portion of the internal member include through-holes 85, 86A, 86B, 87A, and 87B. A distal end of the irrigation tubing 38 terminates and is anchored in the fluid through-hole 85. Distal ends of the thermocouple wires 41 and 45 are fixed in the hole 87A. A distal end of the tip electrode lead wire 40T is anchored in the through-hole 87B The tip electrode lead wire 40 energizes the shell 51 and at least the base portion 83 of the internal member 52. Distal end of each puller wire has a T-anchor, as known in the art. The T-anchors are soldered in diametrically-opposing through-holes 86A 86B so that the puller wires are anchored to the base portion 83 and not a tubing wall which can tear. So anchored in the holes 86A 86B the puller wires provide the catheter with symmetrical bi-directional deflection of the intermediate section 14. The base portion can also include a circumferential lip 106 at the proximal face as an abutment for a proximal end of the shell 51 so as to maintain the gap 102 between the distal end of the tubing portion 80 and the distal end of the shell 51. The lip and the proximal end of the shell 51 can be fixedly joined, for example, by laser welding.

In accordance with another feature of the present invention, the fluid through-hole 85 is aligned with the baffle mid-portion 81 such that the hole 85 faces an edge 90 so fluid exiting the hole 85 impinges on the edge 90 and diffuses around the stem portion 82. This alignment between the hole 85 (and the irrigation tubing 38) and the edge 90, combined with the annular gap 88 provided by the stem portion 82, enables a flow that is more uniform and equal in the radial direction through the flow paths 94 which in turn provides increased turbulence and a more uniform flow rate in the annular space 104 of the cavity 70 and thus more increased convective cooling on the shell 51. Irrigation in the tip electrode is thus more uniform throughout the length of the tip electrode. The internal member thus effectively counters the tendency for the velocity of the fluid entering the tip electrode to carry the fluid to the more distal ports 74 and starve the more proximal ports 74.

The cross-section of the off-axis through hole 85 for the irrigation tubing 38 is elongated, that is, more oval than circular as defined by a greater dimension Y and a lesser dimension X generally perpendicular to greater dimension Y. In the disclosed embodiment of FIG. 9f, the cross-section is elongated with a curvature C, to provide, for example, a kidney-bean or crescent shape cross-section. The present invention recognizes that a cross-section which is at least elongated if not also curved provides a through-hole that can provide greater fluid flow into the tip electrode with less interference with the on-axis location of the internal passage 84 and the sensor cable 48.

Because the irrigation tubing 85 is flexible, e.g., being made of polyurethane, the irrigation tubing 38 readily adapts to the shape of the through-hole 85. As irrigation fluid is delivered by the tubing 38 into the tip electrode 17 through the through-hole 85, it enters and flows into the annular gap 88 at the stem portion 82 where it is dispersed by the baffle portion 81 and flows into the flow channels 94 defined by the edges 90 and corners 92. As the fluid enters the cavity 70 between the tubular portion 80 and the shell 51, it further disperses in the cavity 70 and ultimately leaves the cavity via ports 74. The catheter 10 provides better flow and dispersion of fluid within the tip electrode for improved if not exceptional cooling characteristics during ablation. The tip electrode of the present invention can operate at about 12 ml/minute or lower for wattage below or above 30. The reduction in fluid-loading on the patient in a five or six hour procedure can thus be very significant. Moreover, where the flow rate is regulated by a programmable pump, the flow rate can even be lower for lower wattage.

In an alternate embodiment of FIG. 10, the internal member 52 includes radial projections or fins 110 that extend outwardly from the tubular portion 80 in a direction generally perpendicular to the longitudinal axis 50 of the tip electrode. The fins 110 serve to decrease the velocity of the fluid as it travels distally in the annular region 104 of the cavity 70 in the tip electrode. In FIG. 10, the fins are thin annular discs located at intermittent locations, if not equidistant to each other, along the length of the tubular portion 80. In one embodiment, the fin diameter increases in the proximal direction, so that the effect of decreasing fluid velocity is greatest when the fluid first enters the annular space 104 in the tip electrode 17 for a more uniform dispersion of fluid along the length of the tip electrode and through all ports 74 in the shell 51 to the exterior of the shell.

Also in the embodiment of FIGS. 10 and 10B, the baffle mid-portion 81 has a star-shaped cross-section with a plurality of projections or arms 93 that span outwardly in a uniform radial pattern, with ends in circumferential contact with the neck portion 56 of the shell 51, again forming distinct axial flow paths 94 between the arms. However, it is understood that the present invention also includes a cross-section where there is no circumferential contact between the baffle mid portion 81 and the neck portion 56, such as illustrated in FIG. 10A. There, different but not necessarily distinct axial flow paths or channels 94 are provided, which also facilitate dispersion and flow into the annular space 104 of the tip electrode.

The entirety of the internal member can also constructed of the aforementioned materials of the shell. And where at least the tubular portion 80 is constructed of a conductive metal, including the palladium platinum alloy, the EM sensor is shielded from RF ablation or a stiff plastic such as polyimide. Metal foil can also be used shield the sensor as long as it is electrically connected to the overall electrode housing. The present invention also includes an alternate embodiment where portions of the internal member, for example, tubular portion 80 and the housing 52 are constructed of another material, such as plastic, polyimide, polyurethane or PEBAX, to reduce cost.

A length of the tip electrode from a distal end of the shell to a proximal end of the internal member can range between about 2 mm to 12 mm, and preferably between about to 3 mm to 10 mm.

The ring electrodes 21 which are mounted on the connector tubing 53 can be made of any suitable solid conductive material, such as platinum or gold, preferably a combination of platinum and iridium. The ring electrodes can be mounted onto the connector tubing 53 with glue or the like. Alternatively, the ring electrodes can be formed by coating the tubing 53 with an electrically conducting material, like platinum, gold and/or iridium. The coating can be applied using sputtering, ion beam deposition or an equivalent technique. The number of the ring electrodes on the tubing 53 can vary as desired. The rings may be monopolar or bi-polar. In the illustrated embodiment, there are a distal monopolar ring electrode and a proximal pair of bi-polar ring electrodes. Each ring electrode is connected to a respective lead wire 40R.

Each lead wire 40R is attached to its corresponding ring electrode by any suitable method. A preferred method for attaching a lead wire to a ring electrode involves first making a small hole through the wall of the non-conductive covering or tubing. Such a hole can be created, for example, by inserting a needle through the non-conductive covering and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire around the non-conductive covering a number of times and stripping the lead wire of its own insulated coating on its outwardly facing surfaces.

The tip electrode 17 is electrically connected to a source of ablation energy by the lead wire 40T. The ring electrodes 21 are electrically connected to an appropriate mapping or monitoring system by respective lead wires 40R.

The lead wires 40T and 40R pass through the lumen 30 of the tubing 19 of the deflectable intermediate section 14 and the central lumen of the catheter body 12. The portion of the lead wires extending through the central lumen 18 of the catheter body 12, and proximal end of the lumen 24 can be enclosed within a protective sheath (not shown), which can be made of any suitable material, preferably polyimide. The protective sheath is anchored at its distal end to the proximal end of the intermediate section 14 by gluing it in the lumen 24 with polyurethane glue or the like. Each electrode lead wire has its proximal end terminating in a connector at the proximal end of the control handle 16.

Whereas conventional construction methods build a tip electrode "from the outside in," the present two piece construction allows for construction "from the inside out." That is, the two piece construction of the tip electrode also allows different order or sequences of catheter assembly. For example, the ring electrodes 21 can be mounted on the connector tubing 53 at a stage separate from the assembly of the tip electrode 17. The tubing, puller wires, sensor and the thermocouple can be added to the tip electrode at a later stage or time compared to conventional catheter assembly methods.

Significantly, the two-piece configuration and assembly of the tip electrode 17 allows for testing, evaluation and inspection of the interior of the tip electrode before the tip electrode is fully assembled. One method of assembling the tip electrode includes inserting the sensor 46 and cable 48 into the central passage 84 of the internal member 52 so that the sensor is received in the tubular portion 80 of the internal member (with the sensor's proximal end abutting the stop 106) and the cable 48 extends distally through the central passage 84 and out the proximal face of the base portion 83. Thereafter, the sensor 46 is sealed within the tubular portion 80 by sealant 101 filling the distal end the tubular portion 80. Anchoring and attachment of distal ends of lead wire 40 for the tip electrode, puller wires 36 and thermocouple wires 41, 45 are then made to the base portion 83 of the internal member 52 in the respective holes 86A, 86B, 87A and 87B (as shown, for example, in FIG. 9F) by means including T-bar anchoring and/or soldering. A distal end of the irrigation tubing 38 is then inserted to the elongated hole 85 and affixed by adhesive. It is understood that each of these anchorings and attachments in the holes in the base portion forms a fluid-tight seal so that irrigation fluid cannot escape into the connector tubing 53 proximal the tip electrode 17. After such stages of assembly have been met, the functionality and integrity of the tip electrode, including the tip and ring electrodes, the various electrical, component and fluid junctions and connections, and the various fluid-tight seals can be advantageously tested, evaluated and inspected before the shell is received on the internal member. This feature is another significant advantage over conventional ablation and mapping catheters where testing is done "blind" without easy accessibility to the interior of the tip electrode.

After testing of the tip electrode, the shell 51 can be placed over the internal member 52 centered and aligned by the contact between the corners 92 of the baffle portion 81 and the neck 56 portion of the shell 51. The shell is then attached to the baffle portion via press fit, glue, electrical or laser welding, mechanical deformation, or some other means of joining the two parts. The connector tubing 53 is then be slid over the neck portion 56 and connected to a distal end of the tubing 19 of the deflectable intermediate section 14.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter carrying a position sensor, comprising:
an elongated catheter body;
a tip electrode distal the elongated catheter body, the tip electrode having a longitudinal axis and comprising:
   a shell defining a cavity, the shell having fluid ports;
   an internal member extending into the cavity, the internal member having a portion that generally surrounds the position sensor and positions the position sensor generally centered in the cavity and on-axis with the longitudinal axis of the tip electrode; and
   an annular region extending along the longitudinal axis of the tip electrode between the shell and the internal member, wherein irrigation fluid delivered to the tip electrode is dispersed in the annular region and passes to outside the shell via the fluid ports, the internal member further comprising a baffle portion defining gaps between the internal member and an inner circumferential surface of the shell through which the irrigation fluid travels to reach the annular region.

2. The catheter according to claim 1, wherein the internal member includes a tubular portion, the baffle portion, and a base portion.

3. The catheter according to claim 2, wherein the position sensor is received in the tubular portion.

4. The catheter according to claim 1, wherein the gaps define multiple fluid flow paths that are separate and distinct.

5. The catheter according to claim 1, further comprising at least one annular disk on the portion of the internal member that generally surrounds the position sensor.

6. A catheter carrying a position sensor, comprising:
an elongated catheter body;
a tip electrode distal the elongated catheter body, the tip electrode having a longitudinal axis and comprising:
a shell defining a cavity, the shell having fluid ports;
an internal member extending into the cavity, the internal member having a portion that generally surrounds the position sensor and positions the position sensor generally centered in the cavity and on-axis with the longitudinal axis of the tip electrode;
an annular region extending along the longitudinal axis of the tip electrode between the shell and the internal member, wherein irrigation fluid delivered to the tip electrode is dispersed in the annular region and passes to outside the shell via the fluid ports; and
a plurality of annular disks at different locations along a length of the portion of the internal member that generally surrounds the position sensor.

7. The catheter according to claim 6, wherein a proximal-most annular disk has a diameter greater than a distal-most annular disk.

8. The catheter according to claim 7, wherein diameters of the plurality of annular disks decrease from the proximal-most annular disk to the distal-most annular disk.

9. An ablation catheter carrying a position sensor, comprising:
an elongated catheter body;
a tip electrode distal the elongated catheter body, the tip electrode having a longitudinal axis, and comprising:
a shell defining a cavity and having fluid ports,
an internal member having:
a tubular portion carrying the position sensor centered in the tip electrode and on-axis with the longitudinal axis of the tip electrode,
a base portion, and
a baffle portion defining multiple fluid flow paths; and
an annular region extending along the longitudinal axis of the tip electrode between the shell and the tubular portion of the internal member, wherein irrigation fluid delivered to the tip electrode passes into the annular region through the multiple fluid flow paths of the baffle portion and exits the shell via the fluid ports.

10. The catheter according to claim 9, wherein the shell has a distal portion and a proximal neck portion, wherein the tubular portion carrying the position sensor is positioned in the distal portion, and the base portion is positioned in the neck portion.

11. The catheter according to claim 9, wherein the position sensor is encapsulated in the tubular portion of the internal member.

12. The catheter according to claim 9, wherein the tubular portion is in a generally surrounding relationship to the position sensor.

13. The catheter according to claim 9, wherein the base portion includes an irrigation hole, the hole having an elongated cross-section.

14. The catheter according to claim 9, wherein the base portion includes an irrigation hole and the baffle portion includes an edge, wherein the hole and the edge are aligned.

15. The catheter according to claim 9, further comprising at least one annular disk on the tubular portion of the internal member.

16. The catheter according to claim 15, wherein the at least one annular disk comprises a plurality of annular disks at different locations along a length of the tubular portion of the internal member.

17. The catheter according to claim 16, wherein a proximal-most annular disk has a diameter greater than a distal-most annular disk.

18. The catheter according to claim 17, wherein diameters of the plurality of annular disks decrease from the proximal-most annular disk to the distal-most annular disk.

19. The catheter according to claim 9, wherein the multiple fluid flow paths are separate and distinct.

* * * * *